(12) United States Patent
Cheng et al.

(10) Patent No.: US 9,757,330 B2
(45) Date of Patent: Sep. 12, 2017

(54) RECIPE FOR IN-SITU GEL, AND IMPLANT, DRUG DELIVERY SYSTEM FORMED THEREBY

(71) Applicant: INDUSTRIAL TECHNOLOGY RESEARCH INSTITUTE, Hsinchu (TW)

(72) Inventors: Felice Cheng, Zhubei (TW); Maggie J. M. Lu, Jhudong Township (TW); Yi-Ju Ko, New Taipei (TW); Min-Ying Lin, Hsinchu (TW); Shuen-Hsiang Chou, Zhunan Township (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 16 days.

(21) Appl. No.: 14/488,431

(22) Filed: Sep. 17, 2014

(65) Prior Publication Data

US 2015/0111834 A1    Apr. 23, 2015

Related U.S. Application Data

(60) Provisional application No. 61/892,729, filed on Oct. 18, 2013.

(51) Int. Cl.
| | | |
|---|---|---|
| A61K 38/00 | (2006.01) | |
| C07K 16/00 | (2006.01) | |
| A61K 9/00 | (2006.01) | |
| A61K 47/36 | (2006.01) | |
| A61K 31/00 | (2006.01) | |

(52) U.S. Cl.
CPC .......... *A61K 9/0048* (2013.01); *A61K 9/0024* (2013.01); *A61K 31/00* (2013.01); *A61K 47/36* (2013.01)

(58) Field of Classification Search
None
See application file for complete search history.

(56) References Cited

U.S. PATENT DOCUMENTS

| | | |
|---|---|---|
| 3,587,409 A | 6/1971 | Berge |
| 4,069,014 A | 1/1978 | Pintar |
| 4,933,178 A | 6/1990 | Capelli |
| 4,938,763 A | 7/1990 | Dunn et al. |
| 5,275,760 A | 1/1994 | Johnson |
| 5,350,800 A | 9/1994 | Verhoeven et al. |
| 5,575,815 A | 11/1996 | Slepian et al. |
| 5,702,717 A | 12/1997 | Cha et al. |
| 5,792,469 A | 8/1998 | Tipton et al. |
| 5,990,194 A | 11/1999 | Dunn et al. |
| 6,010,714 A | 1/2000 | Leung et al. |
| 6,311,690 B1 | 11/2001 | Jefferies |
| 6,617,397 B2 | 9/2003 | McNamara et al. |
| 6,703,047 B2 | 3/2004 | Sawhney et al. |
| 6,773,703 B1 | 8/2004 | Ettner et al. |
| 6,818,018 B1 | 11/2004 | Sawhney |
| 6,884,427 B1 | 4/2005 | Barrows |
| 6,923,988 B2 | 8/2005 | Patel et al. |
| 7,235,068 B2 | 6/2007 | Theeuwes et al. |
| 7,241,569 B2 | 7/2007 | Rigler et al. |
| 7,303,756 B1 | 12/2007 | Bodmeier |
| 7,357,947 B2 | 4/2008 | Nimni |
| 7,776,351 B2 | 8/2010 | Benz |
| 7,807,823 B2 | 10/2010 | Moya et al. |
| 7,901,707 B2 | 3/2011 | Allen et al. |
| 7,927,618 B2 | 4/2011 | Bodmeier |
| 8,003,131 B2 | 8/2011 | Badylak |
| 8,008,476 B2 | 8/2011 | Moya et al. |
| 8,092,815 B2 | 1/2012 | Sabesan |
| 8,173,148 B2 | 5/2012 | Dadey et al. |
| 8,173,765 B2 | 5/2012 | Zhu et al. |
| 8,211,938 B2 | 7/2012 | Hedman |
| 8,231,929 B2 | 7/2012 | Sun |
| 8,277,829 B2 | 10/2012 | Jain et al. |
| 8,313,763 B2 | 11/2012 | Margaron et al. |
| 2004/0052761 A1 | 3/2004 | Vernon et al. |
| 2004/0115172 A1 | 6/2004 | Bianchi et al. |
| 2005/0171052 A1 | 8/2005 | Cook et al. |
| 2005/0220982 A1 | 10/2005 | Moya et al. |
| 2006/0121085 A1 | 6/2006 | Warren et al. |
| 2006/0159718 A1 | 7/2006 | Rathenow et al. |
| 2006/0210594 A1 | 9/2006 | Trieu |
| 2006/0239864 A1 | 10/2006 | Ugolin et al. |
| 2009/0022775 A1 | 1/2009 | Champ et al. |
| 2009/0182425 A1 | 7/2009 | Duda et al. |

(Continued)

FOREIGN PATENT DOCUMENTS

| | | |
|---|---|---|
| AU | 2006308534 A1 | 5/2007 |
| BR | PI0710233-0 A2 | 8/2011 |

(Continued)

OTHER PUBLICATIONS

Jia et al. Macromol. Biosci., 2009, 9(2), 140-156.*
Jia et al., Macromol. Biosci., 2009, 9(2), 140-156.*
Elstad et al., Advanced Drug Delivery Reviews, 2009, 61, 785-794.*
Ko et al., Progress in Polymer Science, 2013, 38, 672-701.*
Taiwan Office Action for Appl. No. 103134515 dated Oct. 21, 2015.
Chinese Office Action and Search Report, dated Dec. 5, 2016, for Chinese Application No. 201410552783.4.
Usha et al., "Effect of Hydrogen-Bond-Breaking Reagent (Urea) on the Dimensional Stability of Rat Tail Tendon (RTT) Collagen Fiber," Journal of Applied Polymer Science, vol. 84, 2002, pp. 975-982.
Yang et al., "Refolding Hydrogels Self-Assembled from N-(2-Hydroxypropyl)methacrylamide Graft Copolymers by Antiparallel Coiled-Coil Formation," Biomacromolecules, vol. 7, No. 4, 2006 (Published on the web Mar. 9, 2006), pp. 1187-1195.

(Continued)

*Primary Examiner* — Jeanette Lieb
(74) *Attorney, Agent, or Firm* — Birch, Stewart, Kolasch & Birch, LLP

(57) ABSTRACT

The disclosure provides a recipe for in-situ gel, formed by dissolving at least one polymer and at least one gel prevention agent in a polar solvent to form a solution and placing the solution in a condition for in-situ forming gels. The disclosure also provides an implant and a drug delivery system formed by the recipe.

20 Claims, 4 Drawing Sheets

(56) References Cited

U.S. PATENT DOCUMENTS

| | | |
|---|---|---|
| 2009/0324668 A1 | 12/2009 | Kangasniemi et al. |
| 2010/0035997 A1 | 2/2010 | Broadley et al. |
| 2010/0080836 A1 | 4/2010 | Busch |
| 2010/0203163 A1 | 8/2010 | Allen |
| 2011/0172394 A1 | 7/2011 | Knight et al. |
| 2011/0245172 A1 | 10/2011 | Norton |

FOREIGN PATENT DOCUMENTS

| | | |
|---|---|---|
| BR | PI0710234-8 A2 | 8/2011 |
| CA | 1 266 613 A1 | 3/1990 |
| CA | 1336732 C | 8/1995 |
| CA | 2 599 591 A1 | 9/2006 |
| CA | 2 448 777 C | 9/2009 |
| CN | 1080308 A | 1/1994 |
| CN | 100469790 C | 3/2009 |
| CN | 101400363 A | 4/2009 |
| CN | 102295782 A | 12/2011 |
| DE | 602 13 063 T2 | 11/2006 |
| EP | 0 169 016 A2 | 1/1986 |
| EP | 0 182 483 A1 | 5/1986 |
| EP | 0 242 466 A1 | 10/1987 |
| JP | 3-79061 B2 | 12/1991 |
| JP | 6-72850 B2 | 9/1994 |
| JP | 8-217586 A | 8/1996 |
| JP | 2005-53817 A | 3/2005 |
| JP | 2007-525429 A | 9/2007 |
| JP | 2010-94519 A | 4/2010 |
| TW | 200836778 A | 9/2008 |
| TW | I318885 B | 1/2010 |
| WO | WO 86/00089 A1 | 1/1986 |
| WO | WO 87/06956 A1 | 11/1987 |
| WO | WO 89/04646 A1 | 6/1989 |
| WO | WO 92/16623 A2 | 10/1992 |
| WO | WO 93/07271 A1 | 4/1993 |
| WO | WO 94/19810 A1 | 9/1994 |
| WO | WO 96/17871 A1 | 6/1996 |
| WO | WO 97/26240 A1 | 7/1997 |
| WO | WO 97/36614 A1 | 10/1997 |
| WO | WO 98/15648 A1 | 4/1998 |
| WO | WO 99/07740 A2 | 2/1999 |
| WO | WO 99/08113 A1 | 2/1999 |
| WO | WO 99/23230 A1 | 5/1999 |
| WO | WO 99/30718 A2 | 6/1999 |
| WO | WO 01/08714 A1 | 2/2001 |
| WO | WO 01/08715 A1 | 2/2001 |
| WO | WO 2006/026325 A2 | 3/2006 |
| WO | WO 2006/081279 A2 | 8/2006 |
| WO | WO 2007/010553 A2 | 1/2007 |
| WO | WO 2007/053850 A2 | 5/2007 |
| WO | PCT/2007/02597 | 8/2007 |
| WO | WO 2011/018800 A2 | 2/2011 |
| WO | WO 2011/028031 A2 | 3/2011 |
| WO | PCT/2010/08584 | 9/2011 |
| WO | WO 2012/025582 A2 | 3/2012 |
| WO | WO 2012/175153 A2 | 12/2012 |
| WO | WO 2012/175164 A1 | 12/2012 |

OTHER PUBLICATIONS

Balakrishnan et al., "Evaluation of an in situ forming hydrogel wound dressing based on oxidized alginate and gelatin", Biomaterials 26 (2005), pp. 6335-6342.

Chiu et al., "pH-triggered injectable hydrogels prepared from aqueous N-palmitoyl chitosan: In vitro characteristics and in vivo biocompatibility", Biomaterials 30 (2009), pp. 4877-4888.

De Souza et al., "Biocompatibility of injectable chitosan-phospholipid implant systems", Biomaterials 30 (2009), pp. 3818-3824.

Elstad et al., "OncoGel (ReGel/paclitaxel)—Clinical applications for a novel paclitaxel delivery system", Advanced Drug Delivery Reviews 61 (2009), pp. 785-794.

King et al., "The use of injectable forms of fibrin and fibronectin to support axonal ingrowth after spinal cord injury", Biomaterials 31 (2010), pp. 4447-4456.

Ko et al., "Recent progress of in situ formed gels for biomedical applications", Progress in Polymer Science 38 (2013), pp. 672-701.

Lu et al., "Sucrose Acetate Isobutyrate as an in Situ Forming System for Sustained Risperidone Release", Journal of Pharmaceutical Sciences, vol. 96, No. 12, Dec. 2007, pp. 3252-3262.

Packhaeuser et al., "In situ forming parenteral drug delivery systems: an overview", European Journal of Pharmaceutics and Biopharmaceutics 58 (2004), pp. 445-455.

Patel et al., "Effect of injection site on in situ implant formation and drug release in vivo", Journal of Controlled Release 147 (2010), pp. 350-358.

Rosenblatt et al., "Injectable collagen as a pH-sensitive hydrogel", Biomaterials 1994, vol. 15, No. 12, pp. 985-995.

Ruel-Gariépy et al., "In situ-forming hydrogels-review of temperature-sensitive systems", European Journal of Pharmaceutics and Biopharmaceutics 58 (2004), pp. 409-426.

Smeds et al., "Photocrosslinkable polysaccharides for in situ hydrogel formation", Journal of Biomedical Materials Research, vol. 54, pp. 115-121 (2001).

Tan et al., "Injectable in situ forming biodegradable chitosan-hyaluronic acid based hydrogels for cartilage tissue engineering", Biomaterials 30 (2009), pp. 2499-2506.

Van Tomme et al., "In situ gelling hydrogels for pharmaceutical and biomedical applications", International Journal of Pharmaceutics 355 (2008), pp. 1-18.

* cited by examiner

RECIPE FOR IN-SITU GEL, AND IMPLANT, DRUG DELIVERY SYSTEM FORMED THEREBY

CROSS REFERENCE TO RELATED APPLICATIONS

This application claims the benefit of U.S. Provisional Application No. 61/892,729, filed Oct. 18, 2013, the disclosure of which is hereby incorporated by reference herein in its entirety.

BACKGROUND

Technical Field

The technical field relates to a recipe for in-situ gel, an implant and drug delivery system formed thereby, and a method of in-situ forming gel.

Description of the Related Art

Parenteral administration of drugs as a depot formulation has been used in treatment for certain diseases. In recent studies, polymer-based implants have been deposited under the skin to sustainedly release drugs carried by the implants. Generally, the implants are formed by first mixing the drugs with the carrier polymer and then processing the product to a desired implant shape. The processed implant is then placed under the skin or at a specific site of animals or humans.

Such formed solid implants have been used for various biomedical applications. However, a surgical incision before implantation is required, which raises the probability for infection and decreases interest for the procedure from patients.

Therefore, a novel implant without surgical implantation is in demand. In addition, simplification of the implant process and increased application of implants to various types of tissues are also in demand.

SUMMARY

One embodiment of the disclosure provides a recipe for in-situ gel which comprises at least one polymer, at least one gel prevention agent and at least one polar solvent.

One embodiment of the disclosure provides a method of in-situ forming gels, which comprises the steps of dissolving at least one polymer and at least one gel prevention agent in a polar solvent to form a solution and placing the solution in a condition to allow the gel prevent agent to diffuse out and form the gel in-situ.

One embodiment of the disclosure provides an implant which comprises an in-situ gel formed by the recipe.

One embodiment of the disclosure provides a method of in-situ forming an implant, which comprises dissolving at least one polymer, at least one gel prevention agent and a pharmaceutically active ingredient in a polar solvent to form a solution and placing the solution in a condition to allow the gel prevent agent to diffuse out and form the implant in-situ.

One embodiment of the disclosure provides a drug delivery system which comprises an in-situ gel formed by the recipe.

One embodiment of the disclosure provides a method of in-situ forming a drug delivery system, which comprises dissolving at least one polymer, at least one gel prevention agent and a pharmaceutically active ingredient in a polar solvent to form a solution and placing the solution in a condition to allow the gel prevent agent to diffuse out and form the drug delivery system in-situ.

BRIEF DESCRIPTION OF THE DRAWINGS

The present invention can be more fully understood by reading the subsequent detailed description and examples with references made to the accompanying drawings, wherein.

DETAILED DESCRIPTION

Figure 1A:
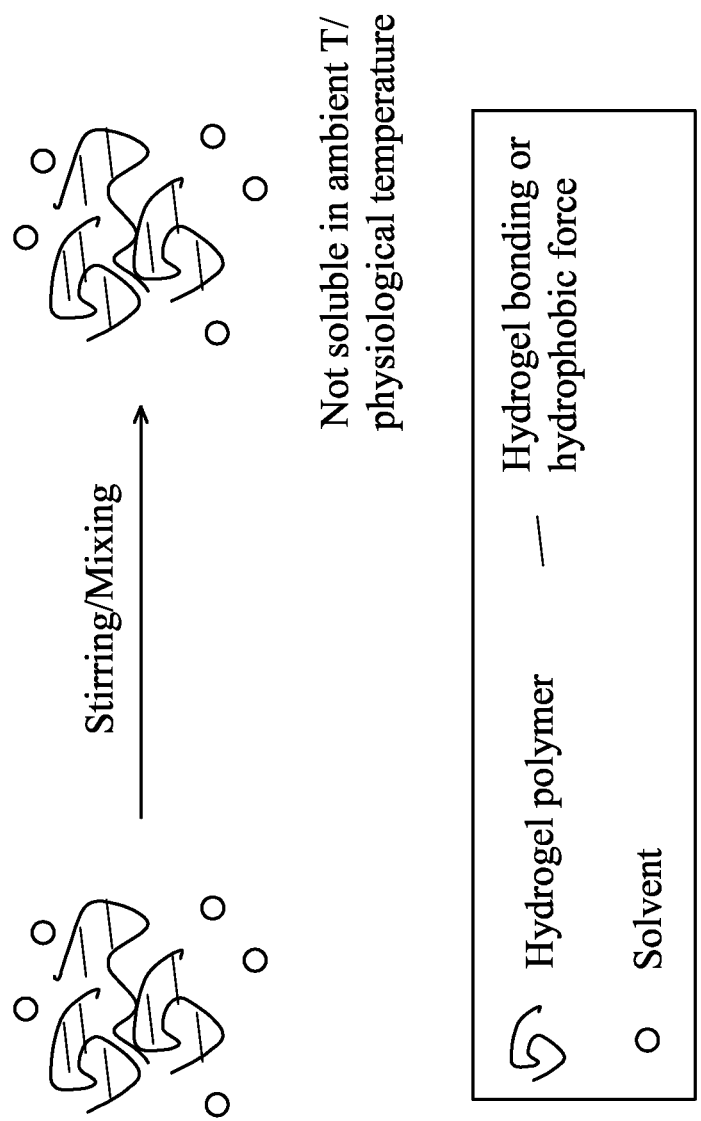
FIG. 1A is a schematic view showing the gelation or precipitation of the polymer in solvents.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The recipe for in-situ gel according to the disclosure comprises at least one polymer, at least one gel prevention agent and at least one polar solvent, wherein the ratio of the polymer and the gel prevention agent is 1:5~1:200 by weight.

The recipe for in-situ gel according to the disclosure can form a gel by the following steps:

dissolving at least one polymer, at least one gel prevention agent and an active ingredient in a polar solvent to form a solution, and mixing an active ingredient in the solution, and placing the solution in a condition to allow the gel prevention agent to diffuse out and form the gel in situ.

The condition may comprise an aqueous environment, living tissues or solvent in which the gel prevention agent is soluble.

The polymer according to the disclosure can be any material which is able to be formed into gels or precipitates without specific limitation. For example, the polymer may be a polymer with an upper critical solution temperature (UCST), polymer complex, synthetic ABA triblock copolymer, zwitterionic homopolymer or a combination thereof.

The polymer with the upper critical solution temperature (UCST) herein refers to a group of thermoresponsive polymers, which is completely miscible above the critical solution temperature. In other words, the polymer with upper critical solution temperature is insoluble in a solvent at low temperature but dissolves when heated. The increase of solubility of the polymer with the upper critical solution temperature in elevated temperature is a result of breaking of inter- or intra-molecular hydrogen bond. In the disclosure, the upper critical solution temperature (UCST) of the polymer solution may comprise hydrogels, such as agarose, agar, carrageenan, gelatin, collagen, agarose-graft-poly[3-dimethyl(methacryloyloxyethyl)ammonium propanesulfonate], poly(N-ethyl-N-methacrylamide), poly(acrylamide-co-acrylic acid), polystyrene-block-poly(methyl acrylate), poly

[6-(acryloyloxymethyl)uracil], poly(2-ethyl-2-oxazoline), poly(2-ethyl-2-oxazoline-stat-2-propyl-2-oxazoline), poly(2-ethyl-N-vinylimidazole), poly(3-ethyl-1-vinyl-2-pyrrolidinone), poly(N-isopropylacrylamide), poly(isobutyl vinyl ether-co-2-hydroxyethyl vinyl ether), poly(vinyl alcohol), poly(N-propylacrylamide), polyvinyl glycine, poly(hydroxyethyl methacrylate), poly(methyl methacrylate), or the like, but are not limited thereto. In one example, agarose aqueous solution with gelation temperature between 20~80° C. is used as a UCST polymer solution.

The polymer complex herein refers polymers or polymer with insoluble macromolecular structure formed by the non-colavent association of polymers having affinity for one another. In more details, the complexes are formed by association of repeating units on different chains (interpolymer complexes) or on separate regions of the same chain (intrapolymer complexes). In the disclosure, the polymer complexes are formed by hydrogen bonding alone or with other non-covalent forces. The hydrogen-bonded complexes herein refer to between polyacids and proton acceptor polymers or block polymers of polyacids and proton acceptor polymers. Polyacids may comprise poly(acrylic acid) and poly(methacrylic acid). Proton acceptor polymers may comprise poly(vinyl esters), polyethyleneoxide, polyacrylamides. The hydrogen-bonded complexes may also comprise chitosan, polynucleotides, collagen, silk fibroin, polyglycine, polyprolines, polypeptides which form helix structure or a combination thereof, but are not limited thereto.

The synthetic ABA triblock copolymer herein refers to a copolymer with a structure consisting of Polymer A, Polymer B and Polymer A in turn. In the disclosure, the biopolymer may comprises a copolymer synthesized with N-(3-(methacryoylamino)propyl)-N,N-dimethyl-N-(3-sulfopropyl)ammonium hydroxide as the A block and 2-(2-methoxtethoxy) ethyl methacrylate as the B block, but are not limited thereto.

The zwitterionic homopolymer in the disclosure refers to a polymer consisting of one kind of zwitterionic monomer. The zwitterionic homopolymer may comprise phosphobetaines, sulfobetaines, carboxybetaines or a combination thereof, but are not limited thereto.

The gel prevention agent in the disclosure refers to compounds which have the ability to prevent the polymer from gelling and diffuse from the polymer as being placed in an aqueous environment or injected into living tissues. In the disclosure, the gel prevention agent may comprise at least one selected from the group consisting of urea, thiourea, N-methylmorpholine N-oxide, guanidinium chloride, lithium bromide, magnesium chloride and sodium dodecyl sulfate, but are not limited thereto.

The ratio of the polymer and the gel prevention agent can be 1:5~1:200 by weight. In one example, the ratio of the polymer and the gel prevention agent can be 1:10~1:100 by weight. In another example, the ratio of the polymer and the gel prevention agent can be 1:20~1:50 by weight.

The polar solvent in the disclosure is not specifically limited, provided that the polymer and the gel prevention agent can be dissolved or miscible in the polar solvent. According to the disclosure, the polar solvent can be biocompatible, such as water, carbonates, hydroxides, esters, ether or amides. In one example, the polar solvent is poly ethylene glycol. The polymer and the gel prevention agent in the polar solvent might be 30~80% by weight based on the total weight of the solution.

Figure 1B:
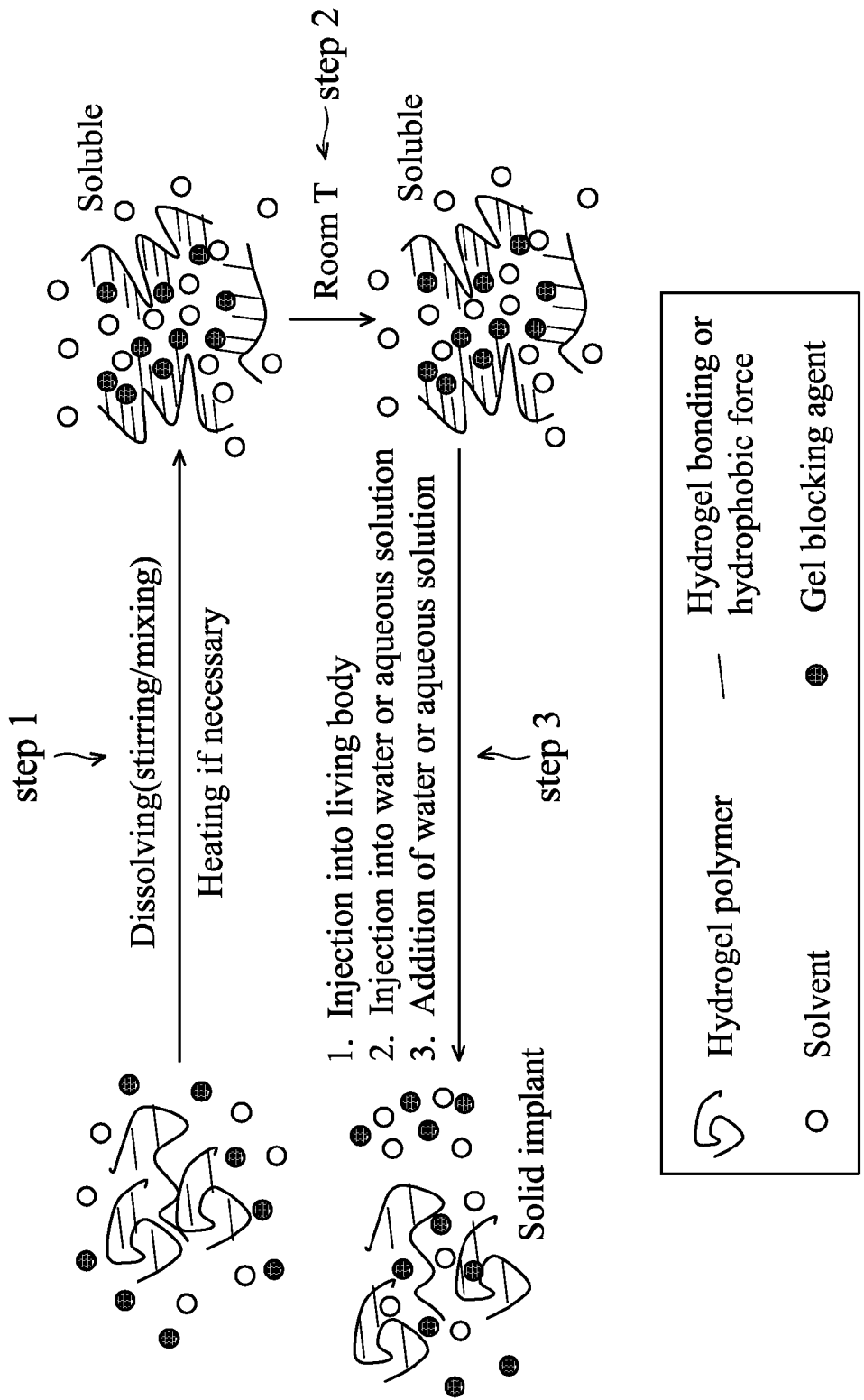
FIG. 1B is a schematic view showing the interaction among the polymer, the gel prevention agent and solvents.

According to the disclosure, the recipe for in-situ gel is in a liquid form at room temperature and normal pressure but becomes gel like when introduced into an aqueous environment, such as animal tissues. Specifically, the polymer and polar solvent of the recipe at room temperature and normal pressure start off in a liquid form but gradually forms into a gel or gel-like substance due to their physical and chemical properties (FIG. 1A). However, when a gel prevention agent is added thereto, the polymer in the recipe does not form into a gel or precipitation, keeping in a liquid form at room temperature and normal pressure (FIG. 1B, Step 2). However, when introduced into an aqueous environment such as animal tissues, the recipe according to the disclosure will form into gels or precipitation (FIG. 1B, Step 3). It is considered that the gel prevention agent interferes with the intramolecular interactions mediated by the non-covalent forces such as hydrogen bond within the polymer and prevents gelation or precipitation from occurring. On the other side, the gel prevention agent is diffused when introduced into aqueous environment so that the interference to the intramolecular interaction of the polymer is decreased or eliminated and thus gel formation occurs.

According to the features of the polymer and the gel prevention agent described above, the recipe for in-situ gel of the disclosure is in a liquid form at room temperature before being placed in an aqueous environment or introduced into animal tissues. Therefore, the recipe for in-situ gel can be introduced into a desired aqueous environment or tissue site and match the introduced site or animal tissue. In one example, the recipe for in-situ gel according to the disclosure can be injected intraperitoneally, intramuscularly, subcutaneously or intraocularly, but it is not limited thereto. In another example, the recipe for in-situ gel of the disclosure can be formulated as eye drops for use in the eyes.

In one embodiment of the disclosure, the recipe for in-situ gel may form an implant when introduced into animal tissues, such as human tissues. In this embodiment, the implant is formed by dissolving the polymer and gel prevention agent in the polar solvent to form a solution and placing the solution in a condition to allow the gel prevent agent to diffuse out. The condition is an aqueous environment, animal tissue or solvent in which the gel prevention agent is soluble. Due to in-situ formation, the implant can be introduced into a desired tissue site, matching the introduced site or tissue without surgery. In addition, because of the properties of the polymer, the implant has enhanced retention and bioavailability, allowing the pharmaceutically active ingredient therein to long-term release. In one example, the recipe for in-situ gel can be injected intraperitoneally, intramuscularly, subcutaneously or intraocularly, but it is not limited thereto. In another example, the recipe for in-situ gel can be formulated as eye drops to form an implant on the surface of eyes.

In another embodiment of the disclosure, the recipe for in-situ gel may form a drug delivery system. In this embodiment, the drug delivery system is formed by dissolving the polymer and gel prevention agent in the polar solvent to form a solution and placing the solution in a condition to allow the gel prevent agent to diffuse out. The condition is an aqueous environment, animal tissue or solvent in which the gel prevention agent is soluble. Due to in-situ formation, the drug delivery system can be introduced into a desired tissue site, matching the introduced site or tissue without surgery. In addition, because of the properties of the polymer, the drug delivery system has enhanced retention and bioavailability, allowing the pharmaceutically active ingredient therein to long-term release. In one example, the recipe for in-situ gel can be injected intraperitoneally, intramuscularly, subcutaneously or intraocularly to form a drug delivery system, but it is not limited thereto. In another example, the recipe for in-situ gel can be formulated as eye drops to from a drug delivery system on the surface of eyes.

The recipe for in-situ gel and the implants and drug delivery system formed thereby may further comprise an active ingredient. The active ingredient may comprise hydrophilic or hydrophobic drugs. For instance, the active ingredient may comprise at least one selected from the group consisting of chemotherapeutics, antibiotics, steroids, antipsychotics, prostaglandin analogs, alpha 2-adrenergic agonists, alpha agonists, growth factors and hormones. To be more specific, the active ingredient comprises paclitaxel, docetaxel, risperidone, paliperidone, latanoprost, bimatoprost, travoprost, brimonidine, apraclonidine, epinephrine, progestoterone, corticosteroids, aldosterones, cortixol, testosterone, estrogen, aminoglycosides, ansamycines, carbacephem, carbapenems, cephalosporine, glycopeptides, lincosamindes, lipopeptides, macrolides, monobactams, nitrofurans, oxazolidonones, penicillins, polypeptides, quinolones, sulfonamides, tetracyclines, butyriophenones, phenothiazine, thioxanthenes, clozapine, olanzapiones, quetiaphine, ziprasidone, amisulpride, asenapine, lioperidone, iloperidone, zotepine, sertindole or lurasidone, but are not limited thereto. According to the disclosure, the recipe for in-situ gel containing the pharmaceutically active ingredient can be in-situ formed at the introduced site and sustainedly release the active ingredient into the environment or the tissue around the introduced site. Therefore, the recipe for in-situ gel containing the active ingredient can be designed as an implant or drug delivery system with the properties of the recipe.

Example 1

3 mg of Bornstein and Traub Type I Collagen from the tail of a rat, 150 mg of urea and 300 μL of deionized water (DI water) were mixed and then stirred for 2 hours in ambient temperature to produce a clear solution. Thereafter, 100 μL of the solution was injected into phosphate buffered saline (PBS) at ambient temperature. A solid gel was thus formed.

Example 2

10 mg of Bornstein and Traub Type I collagen from rat tail was mixed with 150 mg of L-arginine and then 1000 μl of DI water. The solution was then magnetically stirred for 24 hours. After injecting 200 μl of the solution into PBS at ambient temperature, instant gel formation was observed.

Example 3

11.9 mg of Bornstein and Traub Type I collagen from rat tail was mixed with 31.5 mg of L-arginine and then 200 μl of DI water. The solutions was then magnetically stirred and heated to 37° C. for 2 hours. After injecting 200 μl of the solution into PBS at ambient temperature, fiber-fragment gel formation was observed. If the solution was incubated in 37° C. for 24 hours, no gel formation observed after injecting into PBS.

Example 4

2 mg of Bornstein and Traub Type I collagen from rat tail was mixed with 55 mg of urea and then 200 μl of DI water. The solution was then magnetically stirred at ambient temperature for 2 hours and clear solution was observed. After injecting 100 μl of the solution into PBS at ambient temperature and 37° C., gel formation was observed after 2 hours at ambient temperature but not PBS at 37° C.

Example 5

8 mg of Bornstein and Traub Type I collagen from rat tail was mixed with 125 mg of urea and then 250 μl of DI water. The solution was then magnetically stirred at ambient temperature for 24 hours and clear solution was observed. After injecting 100 μl of the solution into PBS at ambient temperature, gel formation was observed after 2 hours. After injecting 100 μl of the solution into PBS at 37° C., fiber-like suspension was observed after 2 hours.

Example 6

3 mg of Bornstein and Traub Type I collagen from rat tail was mixed with 55 mg of urea and then 200 μl of 0.2 mg/ml or 1 mg/ml of calcium chloride aqueous solution. The solution was then magnetically stirred at ambient temperature for 24 hours. Two hours after injecting 100 μl of the solution into PBS at 37° C., fiber-like suspension formation was observed for 1 mg/ml of calcium chloride aqueous solution but not for 0.2 mg/ml of calcium chloride aqueous solution.

Example 7

400 mg of Poly vinyl alcohol with 87-90% hydrolyzed and molecular weight of 70,000 Da and 200 mg of poly ethylene glycol with molecular weight of 4,000 Da were mixed with 1 g of urea and then 1000 μl of DI water of 70° C. was added. The solution was then magnetically stirred at 70° C. for 2 hours. After injecting 100 μl of the solution into PBS at ambient temperature, small particulates formed.

Example 8

33.9 mg of agarose, 603.5 mg of urea and 600 μL of DI water were mixed and then stirred for 2 hours with heat to produce a clear solution. After the solution reached ambient temperature, the solution remained in liquid form. The solution was then injected into DI water and a solid gel was formed.

Example 9

29.26 mg of agarose, 2000 mg of N-Methylmorpholine N-oxide (NMMO) and 600 μL of DI water were mixed and then stirred for 2 hours at 50-70° C. A clear solution was formed, indicating dissolution of agarose. The solution remained in liquid form after the temperature returned back to ambient temperature. The solution was then injected into DI water and a solid gel was formed.

Example 10

44.4 mg of agarose, 1000 mg of urea and 1000 μL of DI water were mixed and then stirred for 2 hours at 40-50° C. A transparent solution was formed, indicating dissolution of agarose. The solution remained in liquid form after the temperature reached ambient temperature. Thereafter, 200 μL of the solution each was intramuscularly (thigh) and intraperitoneally injected into a Sprague Dawley Rat. The rat was sacrificed 7 days after the injection and gels formed in the thigh and abdomen.

Example 11

Figure 2:
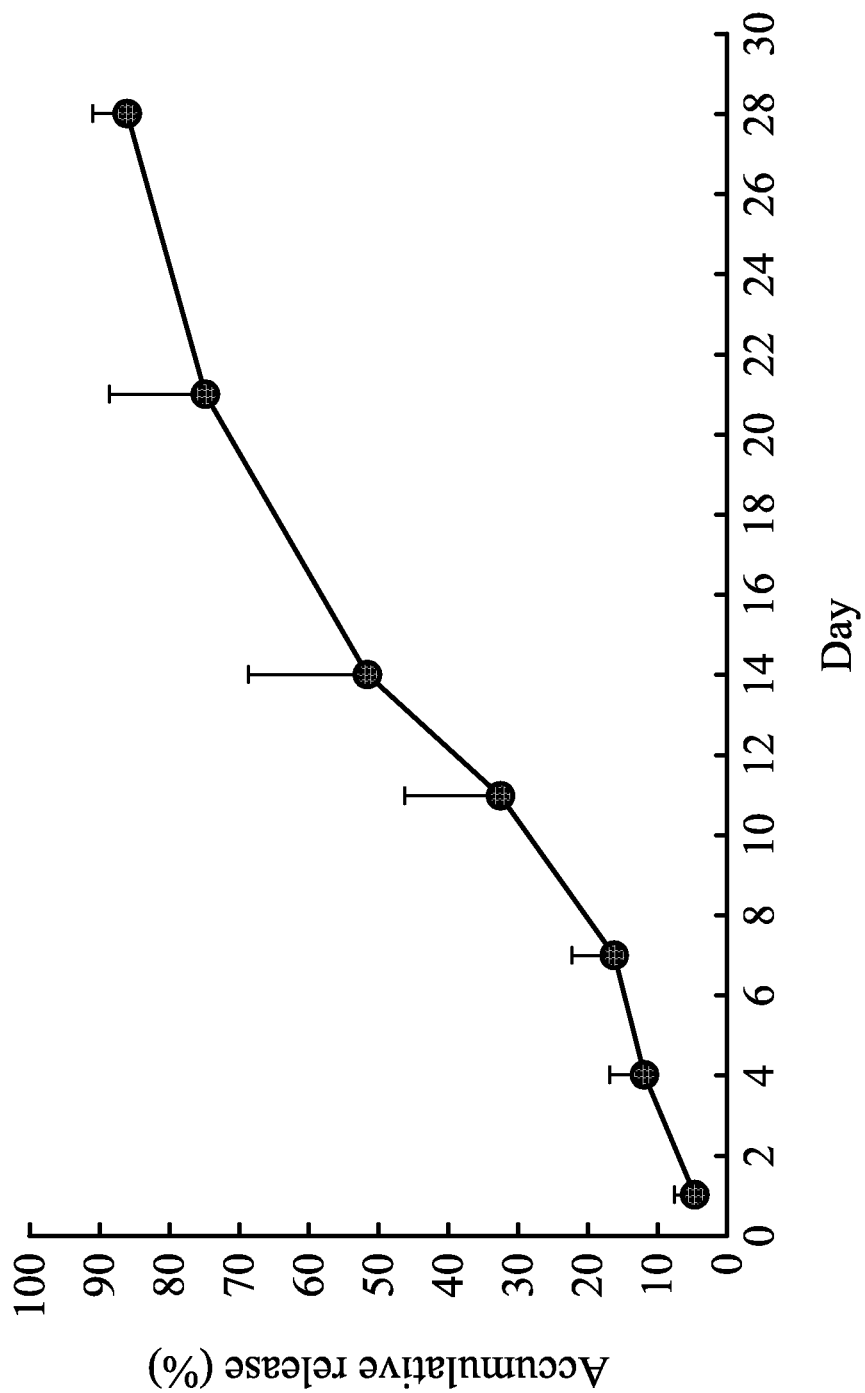
FIG. 2 is a diagram showing an in-vitro release of risperidone from the implant in one example of the disclosure.

450 mg agarose, 9000 mg urea and 9 ml of DI water were stirred at 45-50° C. for 2 hours to prepare a stock solution. 800 μl of the stock solution was mixed with 200 μl of DI water containing dispersed risperidone (20 mg/ml). Then, 150 μl of the solution was added into 12-well Millicells and immersed the insert into 7.5 ml of PBS. The PBS solution was taken out at designated time point and replaced with fresh PBS. The concentration of risperidone was measured via HPLC. The release profile of risperidone from the in-situ hydrogel reached 86% on the 28 day (FIG. 2).

Example 12

Figure 3:
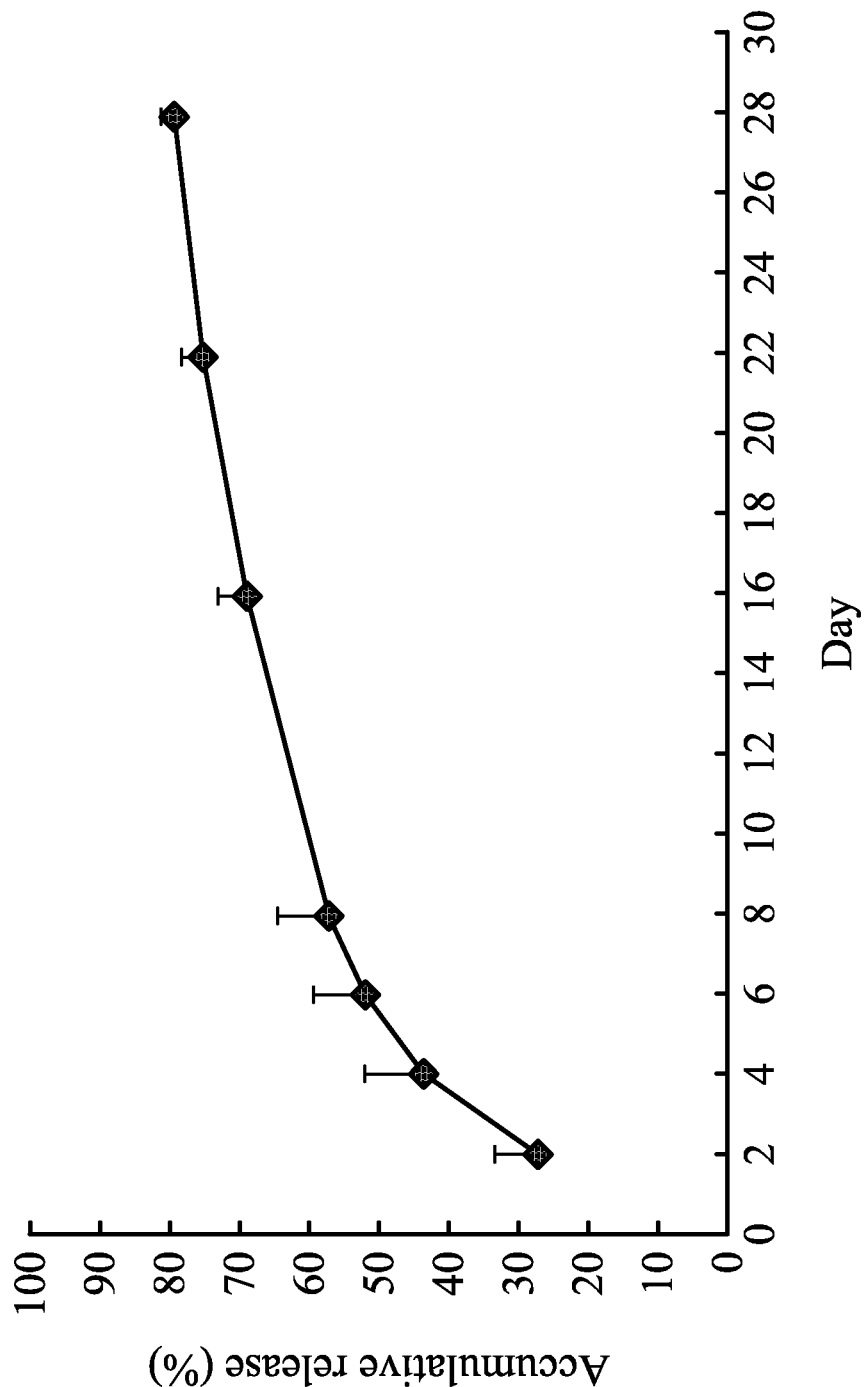
FIG. 3 is a diagram showing an in-vitro release of bovine serum albumin (BSA) from the implant in one example of the disclosure.

150 mg agarose, 3000 mg urea and 3 ml of DI water were stirred at 45-50° C. for 2 hours to prepare a stock solution. 3920 μl of the stock solution was mixed with 80 μl of 250 mg/ml bovine serum albumin (BSA). 500 μl of the solution was injected into a 15-ml conical tube. Then, 5 ml of PBS was added into the tube and the solution was taken out at a designated time point with replacement of fresh PBS. The release of BSA from the in-situ hydrogel reached 79% on the 14 day (FIG. 3).

Example 13

19.65, 29.26, 32.91 and 39.59 mg of agarose were respectively mixed with 2000 mg of N-Methylmorpholine N-oxide (NMMO) and then 600 μl of DI water was added into each sample. The solutions were then magnetically stirred and heated for 2 hours. The solutions were then brought to ambient temperature and no gelation was observed after a day. After injecting 200 μl of the sample into 10 ml of a warm PBS solution (~37° C.), gel formation occurred.

Example 14

32.91 mg of agarose was mixed with 2, 1.5 and 1 g of N-Methylmorpholine N-oxide (NMMO) separately and then 600 μl of DI water was added. The solutions were then magnetically stirred and heated for 2 hours. The solutions were then brought to ambient temperature. The solution containing 1.5 g or 1 g NMMO formed into gel after a day, but the solution containing 2 g NMMO did not. After injecting 200 μl of the solution containing 2 g NMMO into 10 ml of a warm PBS solution (~37° C.), gel formation occurred.

Example 15

11 mg of agarose, 2 g of NMMO and 0.2 ml DI water were magnetically stirred and heated for 2 hours. The solution did not completely dissolve after 2 hours and an opaque gel was observed after being stored in ambient temperature for a day.

Example 16

13 mg of agarose, 2 g of NMMO and 0.6 ml DI water were magnetically stirred and heated for 2 hours. The solution was clear and no gel was formed after being stored in ambient temperature for a day. Thereafter, after being injected into an excess warm PBS solution (~37° C.), gel formation occurred.

Example 17

16 mg of agarose, 2 g of NMMO and 1.2 ml DI water were magnetically stirred and heated for 2 hours. The solution was clear and a gel was formed after being stored in ambient temperature for a day.

Example 18

900, 750, 600, 300 mg of urea were mixed with 33 mg of agarose separately and 0.6 ml of DI water was added. The solutions were then magnetically stirred and heated for 2 hours and then stored in ambient temperature for a day.

Among the solutions, the solution containing 900 mg of urea showed precipitates, the solution containing 750 mg of urea was gelled, and the solution containing 600 mg or 300 mg of urea remained in a solution state and formed gels after being injected into warm PBS.

Example 19

1.8 g of agarose, 36 g of urea and 36 ml of DI water were mixed with magnetic stirring in 50° C. water for 24 hours. Air bubbles were removed via centrifugation with 1500 rpm for 5 minutes. 3 ml of the solution was added into a 6-well plate, wherein the bottom of the plate was covered with a parafilm. Then 12 ml (5x), 7.5 ml (2.5x), 3 ml (1x) or 1.5 ml (0.5x) of DI water were added respectively to different wells. The plate was kept in ambient temperature for a day before rheology characterization. The measurement were carried out with a parallel plate having a diameter of 25 mm under 4.981 Pa with 1 rad/s of angular frequency at 37° C. The results are shown in the following table.

TABLE 1

| Dilution folds | Storage modulus Pa | Loss modulus Pa | Complex viscosity Pa · s | Dynamic viscosity Pa· s |
|---|---|---|---|---|
| 5x | 13722.85 | 714.7855 | 2187.035 | 113.7615 |
| 2.5x | 23353.6 | 1501.13 | 3724.81 | 238.9115 |
| 1x | 311.3165 | 107.4936 | 52.4247 | 17.1081 |
| 0.5x | 1.398325 | 2.73888 | 0.507285 | 0.435905 |

As shown in Table 1, the storage modulus was greatly larger than the loss modulus for all samples except for the sample with the 0.5x dilution fold. The sample with the gel shapes of the 0.5x dilution fold did not hold and showed a very low viscosity, indicating that the dilution fold of the sample might be the limit for in-situ forming gels.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A composition, comprising
   at least one polymer,
   at least one gel prevention agent and
   at least one polar solvent,
   wherein a ratio of the polymer and the gel prevention agent is 1:5~1:200 by weight,
   wherein the gel prevention agent diffuses from the polymer when the composition is placed in an aqueous environment or a living tissue and thereby an in-situ gel is formed,
   wherein the polymer comprises a polymer with an upper critical solution temperature (UCST), biopolymer, synthetic ABA triblock copolymer, zwitterionic homopolymer or a combination thereof, and wherein the synthetic ABA triblock copolymer comprises a copolymer synthesized with N-(3-(methacryoylamino)propyl)-N,N-dimethyl-N-(3-sulfopropyl)ammonium hydroxide as the A block and 2-(2-methoxtethoxy) ethyl methacrylate as the B block, or wherein the zwitterionic homopolymer comprises phosphobetaines, sulfobetaines, carboxybetaines, or a combination thereof.

2. The composition as claimed in claim 1, wherein the polymer with the upper critical solution temperature (UCST) comprises agarose, agar, gelatin, collagen, agarose-graft-poly[3-dimethyl (methacryloyloxyethyl) ammonium propanesulfonate], poly(N-ethyl-N-methacrylamide), poly(acrylamide-co-acrylic acid), polystyrene-block-poly(methyl acrylate), poly[6-(acryloyloxymethyl)uracil], poly(-ethyl-2-oxazoline), poly(2-ethyl-2-oxazoline-stat-2-propyl-2-oxazoline), poly(-ethyl-N-vinylimidazole), poly(3-ethyl-1-vinyl-2-pyrrolidinone), poly(N-isopropylacrylamide), poly(isobutyl vinyl ether-co-2-hydroxyethyl vinyl ether), poly(vinyl alcohol), poly(N-propylacrylamide), polyvinyl glycine, poly(hydroxyethyl methacrylate), poly(methyl methacrylate).

3. The composition as claimed in claim 1, wherein the biopolymer comprises alginate, chitosan, polynucleotides, collagen, polypeptides, proteins, or a combination thereof.

4. The composition as claimed in claim 1, wherein the gel prevention agent comprises at least one selected from the group consisting of urea, thiourea, N-methylmorpholine N-oxide, guanidinium chloride, magnesium chloride and sodium dodecyl sulfate.

5. The composition as claimed in claim 1, wherein the polar solvent is biocompatible.

6. The composition as claimed in claim 5, wherein the polar solvent comprises at least one selected from the group consisting of water, carbonates, hydroxides, esters, ether and amides.

7. The composition as claimed in claim 5, wherein the polar solvent is poly ethylene glycol.

8. The composition as claimed in claim 1, wherein the polymer and the gel prevention agent in the composition is 30~80% by weight.

9. The composition as claimed in claim 1, further comprising a pharmaceutically active ingredient.

10. The composition as claimed in claim 9, wherein the pharmaceutically active ingredient comprises at least one selected from the group consisting of chemotherapeutics, antibiotics, steroids, antipsychotics, prostaglandin analogs, alpha 2-adrenergic agonists, alpha agonists, growth factors and hormones.

11. The composition as claimed in claim 9, wherein the pharmaceutically active ingredient comprises paclitaxel, docetaxel, risperidone, paliperidone, latanoprost, bimatoprost, travoprost, brimonidine, apracolonidine, epinephrine, progestoterone, corticosteroids, aldosterones, cortisol, testosterone, estrogen, aminoglycosides, ansamycines, carbacephem, carbapenems, cephalosporine, glycopeptides, lincosamindes, lipopeptides, macrolides, monobactams, nitrofurans, oxazolidonones, penicillins, polypeptides, quinolones, sulfonamides, tetracyclines, butyriophenones, phenothiazine, thioxanthenes, clozapine, olanzapiones, quetiaphine, ziprasidone, amisulpride, asenapine, lioperidone, iloperidone, zotepine, sertindole or lurasidone.

12. The composition as claimed in claim 9, wherein the composition is injected intraperitoneally, intramuscularly, subcutaneously or intraocularly.

13. The composition as claimed in claim 9, wherein the composition is formulated as eye drops.

14. An implant, comprising an in-situ gel formed by the composition as claimed in claim 1.

15. A drug delivery system, comprising an in-situ gel formed by the composition as claimed in claim 1.

16. The drug delivery system as claim in claim 15, further comprising an pharmaceutically active ingredient selected from the group consisting of paclitaxel, docetaxel, risperidone, paliperidone, latanoprost, bimatoprost, travoprost, brimonidine, apracolonidine, epinephrine, progestoterone, corticosteroids, aldosterones, cortisol, testosterone, estrogen, aminoglycosides, ansamycines, carbacephem, carbapenems, cephalosporine, glycopeptides, lincosamindes, lipopeptides, macrolides, monobactams, nitrofurans, oxazolidonones, penicillins, polypeptides, quinolones, sulfonamides, tetracyclines, butyriophenones, phenothiazine, thioxanthenes, clozapine, olanzapiones, quetiaphine, ziprasidone, amisulpride, asenapine, lioperidone, iloperidone, zotepine, sertindole and lurasidone.

17. The composition as claimed in claim 1, wherein the composition exists in liquid form at room temperature and normal pressure, and when the composition is introduced into an aqueous environment or a living tissue, the composition forms a gel.

18. A composition, comprising at least one polymer, at least one gel prevention agent and at least one polar solvent, wherein a ratio of the polymer and the gel prevention agent is 1:5~1:200 by weight, and wherein the gel prevention agent is diffused from the polymer as placing the composition within the aqueous environment or living tissues and thereby an in-situ gel is formed, wherein the composition further comprising a pharmaceutically active ingredient, and wherein the composition is formulated as eye drops.

19. The composition as claimed in claim 18, wherein the pharmaceutically active ingredient comprises at least one selected from the group consisting of chemotherapeutics, antibiotics, steroids, antipsychotics, prostaglandin analogs, alpha 2-adrenergic agonists, alpha agonists, growth factors and hormones.

20. The composition as claimed in claim 18, wherein the pharmaceutically active ingredient comprises paclitaxel, docetaxel, risperidone, paliperidone, latanoprost, bimatoprost, travoprost, brimonidine, apracolonidine, epinephrine, progestoterone, corticosteroids, aldosterones, cortisol, testosterone, estrogen, aminoglycosides, ansamycines, carbacephem, carbapenems, cephalosporine, glycopeptides, lincosamindes, lipopeptides, macrolides, monobactams, nitrofurans, oxazolidonones, penicillins, polypeptides, quinolones, sulfonamides, tetracyclines, butyriophenones, phenothiazine, thioxanthenes, clozapine, olanzapiones, quetiaphine, ziprasidone, amisulpride, asenapine, lioperidone, iloperidone, zotepine, sertindole or lurasidone.

* * * * *